United States Patent
Mabotuwana et al.

(10) Patent No.: US 10,474,742 B2
(45) Date of Patent: Nov. 12, 2019

(54) AUTOMATIC CREATION OF A FINDING CENTRIC LONGITUDINAL VIEW OF PATIENT FINDINGS

(71) Applicant: KONINKLIJKE PHILIPS N.V., Eindhoven (NL)

(72) Inventors: Thusitha Dananjaya De Silva Mabotuwana, Yonkers, NY (US); Merlijn Sevenster, Chicago, IL (US); Joost Frederik Peters, Utrecht (NL); Yuechen Qian, Briarcliff Manor, NY (US); Adam Randolph Travis, Chicago, IL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 688 days.

(21) Appl. No.: 15/103,913

(22) PCT Filed: Dec. 11, 2014

(86) PCT No.: PCT/IB2014/066811
§ 371 (c)(1),
(2) Date: Jun. 13, 2016

(87) PCT Pub. No.: WO2015/092633
PCT Pub. Date: Jun. 25, 2015

(65) Prior Publication Data
US 2016/0314278 A1    Oct. 27, 2016

Related U.S. Application Data

(60) Provisional application No. 61/918,864, filed on Dec. 20, 2013.

(51) Int. Cl.
*G16H 15/00* (2018.01)
*G06F 17/24* (2006.01)
(Continued)

(52) U.S. Cl.
CPC .......... *G06F 17/241* (2013.01); *G06F 17/272* (2013.01); *G06F 17/2765* (2013.01); *G06F 19/321* (2013.01); *G16H 15/00* (2018.01)

(58) Field of Classification Search
CPC .............................. G06F 17/241; G16H 15/00
See application file for complete search history.

(56) References Cited

U.S. PATENT DOCUMENTS 6,785,410 B2   8/2004  Vining et al.
7,949,166 B2   5/2011  Moriya et al.
(Continued)

FOREIGN PATENT DOCUMENTS

CN   101452503 A    6/2009
JP   H11312200 A   11/1999
(Continued)

OTHER PUBLICATIONS

Mabotuwana, T. et al. "Using Image References in Radiology Reports to Support Enhanced Report-to-Image Navigation"., AMIA Annual Symposium, 2013.
(Continued)

*Primary Examiner* — John A Pauls

(57) ABSTRACT

A system for creating a longitudinal view of patient findings includes a natural language processing engine which extracts clinical findings from a clinical document. A temporal resolution engine determines which other clinical documents the clinical findings belong to. A visualization graphical user interface indicates the correlation of the clinical findings between the clinical document and the other clinical documents. The natural language processing engine also links one or more images to the clinical findings.

16 Claims, 12 Drawing Sheets

(51) Int. Cl.
    *G06F 19/00*     (2018.01)
    *G06F 17/27*     (2006.01)

(56)         References Cited

U.S. PATENT DOCUMENTS

| | | | |
|---|---|---|---|
| 2002/0131625 A1* | 9/2002 | Vining | G06F 19/321 |
| | | | 382/128 |
| 2011/0196886 A1 | 8/2011 | Ho et al. | |
| 2011/0202572 A1 | 8/2011 | Ho et al. | |
| 2012/0130223 A1 | 5/2012 | Reicher | |
| 2013/0024208 A1* | 1/2013 | Vining | A61B 6/467 |
| | | | 705/3 |
| 2013/0035957 A1 | 2/2013 | Gossler et al. | |
| 2013/0254225 A1 | 9/2013 | Sugihara | |

FOREIGN PATENT DOCUMENTS

| | | |
|---|---|---|
| JP | 2008250751 A | 10/2008 |
| JP | 2013527503 A | 6/2013 |

OTHER PUBLICATIONS

Sevenster, M. "Classifying Measurements in Dictated", Free-text Radiology Reports, LNCS 7885, 2013.

* cited by examiner

| Report fragment, January 1 | Report fragment, May 12 | Report fragment, July 2 |
|---|---|---|
| LIVER, BILIARY TRACT: Probable diffuse fatty liver. Subtle hypodense soft tissue along the subcapsular portion of the liver segment 7 measures 1.1 x 2.7 cm (series 5, image 22). Previously 3.2 x 1.3 cm. Length of the liver is normal.<br><br>SPLEEN: Lesion along the anterior aspect of the spleen measures 3.2 x 2.9 cm cyst. Previously 2 x 1.5 cm. Lesion more caudally in the spleen measures 2.5 x 1.6 cm, previously 2.3 x 1.1 cm. | LIVER, BILIARY TRACT: Probable diffuse fatty infiltration. Stable, subtle hypoattenuating subcapsular lesion within segment 7 measures 2.7 x 1.1 cm. This is unchanged (series 5, image 26).<br><br>SPLEEN: Hypoattenuating lesion within the anterior aspect of the spleen measures 3.9 x 3.8 cm (series 3, image 28). This has increased in size, previously measuring 2.9 x 3.2 cm (series 3, image 19). The more caudal hypoattenuating splenic lesion measures 2.4 x 3.0-cm. This has slightly increased in size, previously measuring 2.5 x 1.6 cm. | LIVER, BILIARY TRACT: Probable hepatic steatosis. Hypodense lesion within segment 7 of the liver now measures 3.5 x 1 cm, previously measuring 2.7 x 1.1 cm (series 5, image 26). No new lesions are identified. Status-post cholecystectomy.<br><br>SPLEEN: Homogeneously hypodense lesion within the anterior aspect of the spleen measures 4 x 4 cm (series 3, image 32), previously measuring 3.9 x 3.8 cm (series 3, image 28). More caudal splenic lesion measures 2.9 x 2.2 cm, previously measuring 2.4 x 3 cm. |

FIG. 4

AUTOMATIC CREATION OF A FINDING CENTRIC LONGITUDINAL VIEW OF PATIENT FINDINGS

CROSS-REFERENCE TO PRIOR APPLICATIONS

This application is the U.S. National Phase application under 35 U.S.C. § 371 of International Application No. PCT/IB2014/066811, filed on Dec. 11, 2014, which claims the benefit of U.S. Provisional Application No. 61/918,864, filed on Dec. 20, 2013. These applications are hereby incorporated by reference herein.

The present application relates generally to the automatic creation of a finding-centric longitudinal view of patient findings. It finds particular application in conjunction with extracting measurements and image references from narrative radiology reports and registering the measurements and image references across other radiology reports and will be described with particular reference thereto. However, it is to be understood that it also finds application in other usage scenarios and is not necessarily limited to the aforementioned application.

On a routine basis, radiologists work with an increasing number of studies to diagnose and treat patients in an optimal manner. Patients, especially ones with cancers, frequently undergo imaging exams and over time accumulate many studies, and thereby reports, in their medical records. Each time a new study needs to be read, radiologists typically open one or more prior reports to understand the status of the patient's findings and establish clinical context. Establishing clinical context is non-trivial, especially for complex patients with multiple findings that have progressed over many years, observed across multiple studies. Determining the progression of a finding over time is currently performed manually where the radiologist would read through one or more prior reports, which are free text and narrative by nature, and then manually compare the corresponding findings.

Further, radiology reports often contain measurements and references to particular images when describing findings, for instance, "Neurofibroma in the superior right extraconal space (series 5, image 104) measuring approximately 17 mm." A problem in the current workflow is the requirement to determine the progression of findings over time by manually and mentally linking findings across reports. Additionally, in current diagnostic radiology workflow, when observing a finding, the radiologist needs to know if the finding has been observed before and if it has been diagnosed. Specifically, when a radiologist identifies a finding, the radiologist is interested in finding out if the finding has been identified on a previous exam and/or if the identified finding has been "called," i.e., if it was diagnosed before (as a "cyst" or "metastatic tumor" for instance). For example, it is possible that a finding has previously been identified but not diagnosed. In such instances, the radiologist will simply report on the finding's imaging characteristics (e.g., "hypodense lesion"). In the current workflow, to obtain information on the previous identification and/or diagnosis, the radiologist has to retrieve the report(s) of the relevant prior exam(s), scan it for pertinent sections, and extract the relevant information. Since reports are usually on a different monitor than image studies, this requires the radiologist to change his focus from one monitor to the other. This slows down workflow and is fatiguing.

Additionally, radiologists describe lesions in quantitative (e.g., measurements) and qualitative terms (e.g., "stable", "decreased", "increased"). Both quantitative and qualitative assessments are used by downstream consumers. In the case of measurable lesions in the oncology setting, Response Evaluation Criteria In Solid Tumors (RECIST) guidelines define their relationship. For example, an interval change of more than 20% (in longest dimension) is considered "progression". However, quantitative and qualitative assessments may go astray for several reasons. For example, existing guidelines for defining interval change are not integrated in the workflow. Consequently, different radiologists may use different terminology to describe the same quantitative change. A scout investigation was conducted to plot quantitative data (in terms of interval change) against corresponding qualitative assessments from a large database of radiology reports. All sentences that were selected include two measurements (underlined), for example: "Reference subcarinal mass indistinguishable from the esophagus (series 3 image 40) measures 2.8×2 cm (previously 3.5×2.1 cm) and continues to decrease in size of multiple priors." Interval changes in multi-dimensional measurements were taken as the changes in these measurements' geometric means in order to compensate for varying numbers of reported dimensions. For example, the geometric surfaces defined by the two sets of measurements above are 560 mm$^2$ and 735 mm$^2$, respectively. By comparing geometric means, the interval change is: 0.87 ($\sqrt{(560/735)}$). Using string matching techniques, the qualitative assessments made by the radiologist were determined. For instance, the sample sentence above would be considered "decreased" as it contains the keyword "decrease". The results of the analysis are shown in the diagram of FIG. 1. As shown, there is considerable overlap between interval changes considered decreased and stable on the one hand, and interval changes considered stable and increased on the other hand.

Another problem with quantitative and qualitative assessments is the accumulation of minimal change. For example, if a lesion grows slowly over time, it can be described as stable between two exams even though it displays significant growth over a larger number of exams that span a two-year interval. This information can be retrieved from such an early exam or its report (given that the lesion is present then), but this procedure is time-consuming and radiologists will generally not do it for each and every lesion that is reported stable. If measurement data is available in a structured manner, it can be consulted in an appropriate user interface. However, even though this might be more convenient than looking up exams, it still requires the radiologist to switch his/her attention to another information management system.

Another problem exists with information consumption on a single screen system such as a tablet. The information contained in the qualitative and quantitative description of a lesion will generally be created in a radiology picture archiving and communication system (PACS) workstation viewing environment—with sizeable diagnostic monitors that have plenty of real estate for hanging multiple images of the same lesion at different time-points creating a convenient 'visual' overview of a lesion's progression. Consumption of the information by referring physicians takes place on devices with a single screen including tablets and laptops. This creates a challenge in conveying the information contained in the measurements, images, and qualitative descriptors over time in an as-rich-as-possible yet concise way.

The present application also provides new and improved methods and systems which overcome the above-referenced problems and others.

In accordance with one aspect, a system for creating a longitudinal view of patient findings is provided. The system includes a natural language processor engine which extracts clinical findings from a clinical document. A temporal resolution engine determines which other clinical documents the clinical findings belong to. A visualization graphical user interface indicates the correlation of the clinical findings between the clinical document and the other clinical documents. The natural language processor engine also links one or more images to the clinical findings.

In accordance with another aspect, a method for creating a longitudinal view of patient findings is provided. The method including extracting clinical findings from a clinical document, determining which other clinical documents the clinical findings belong to, indicating the correlation of the clinical findings between the clinical document and the other clinical documents on an interface, and linking one or more images to the clinical findings.

In accordance with another aspect, a system for creating a longitudinal view of patient findings is provided. The system including one or more processor(s) programmed to extract clinical findings from a clinical document, determine which other clinical documents the clinical findings belong to, indicate the correlation of the clinical findings between the clinical document and the other clinical documents on an interface, and link one or more images to the clinical findings.

One advantage resides in extracting and registering measurements and image references from prior radiology reports.

Another advantage resides in extracting and displaying relevant information from prior radiology reports.

Another advantage resides in determining and displaying interval change in radiology findings in prior radiology reports.

Another advantage resides in establishing clinical context and potentially improving workflow efficiency.

Another advantage resides in improving radiologists' viewing and interpretation experience.

Another advantage resides in tracking discordant patient cases.

Another advantage resides in improving clinical workflow.

Another advantage resides in improving patient care.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 4 illustrates an exemplary embodiment of a longitudinal view of patient findings interface generated by the clinical support system according to aspects of the present application.

The present application provides a system and method which automatically creates a finding-centric longitudinal view of a patient by extracting measurements and image references from radiology reports and registering the measurements and image references across previous radiology reports. Specifically, the measurements and image references are registered across radiology reports to create a finding-centric longitudinal view for a patient which are used to establish clinical context, as well as facilitate direct navigation to the corresponding key images, resulting in workflow efficiency gains. The present application also provides a system and method for extracting narrative content from prior radiology reports to identify a finding that has been identified on a previous exam and/or identify if a finding has been diagnosed previously. The present application also provides a system and method which provides an assessment of the interval change of measured findings in previous radiology reports and displays the interval change in a consistent guideline-compliant manner.

Figure 1:
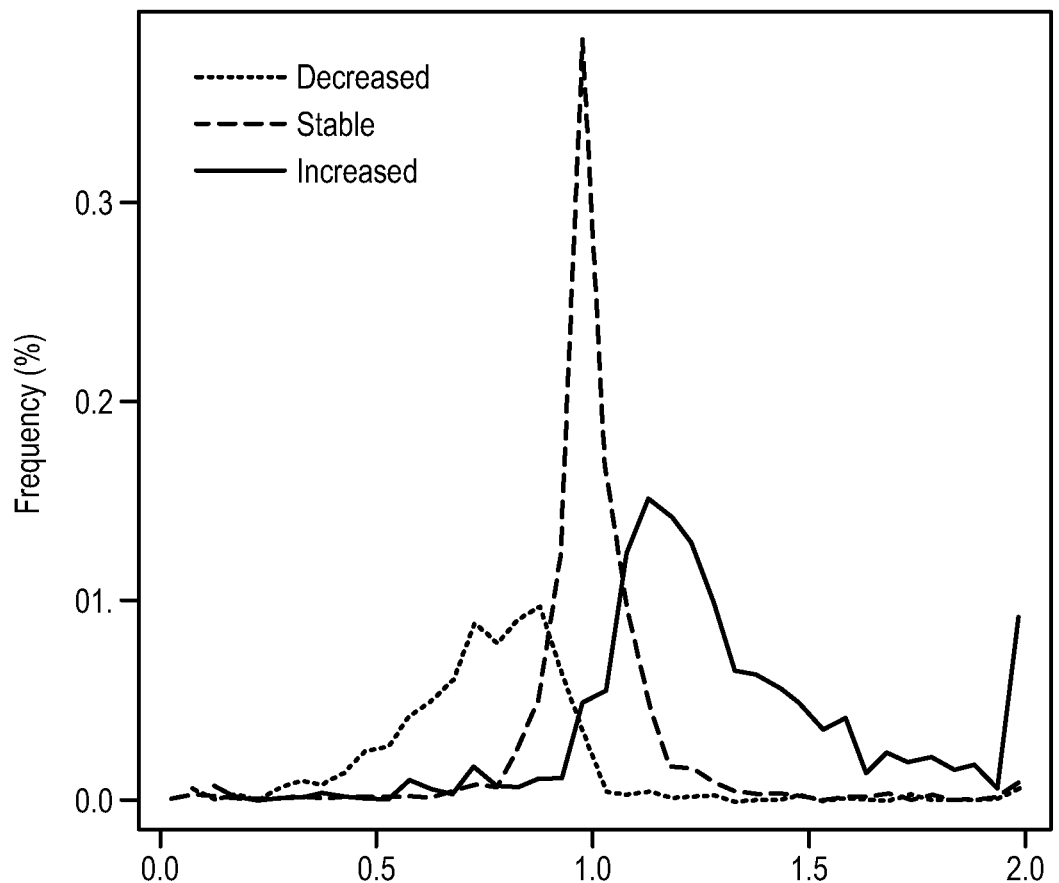
FIG. 1 illustrates a diagram of results of an analysis of the interval change in terminology guidelines according to aspects of the present application.
Figure 2:
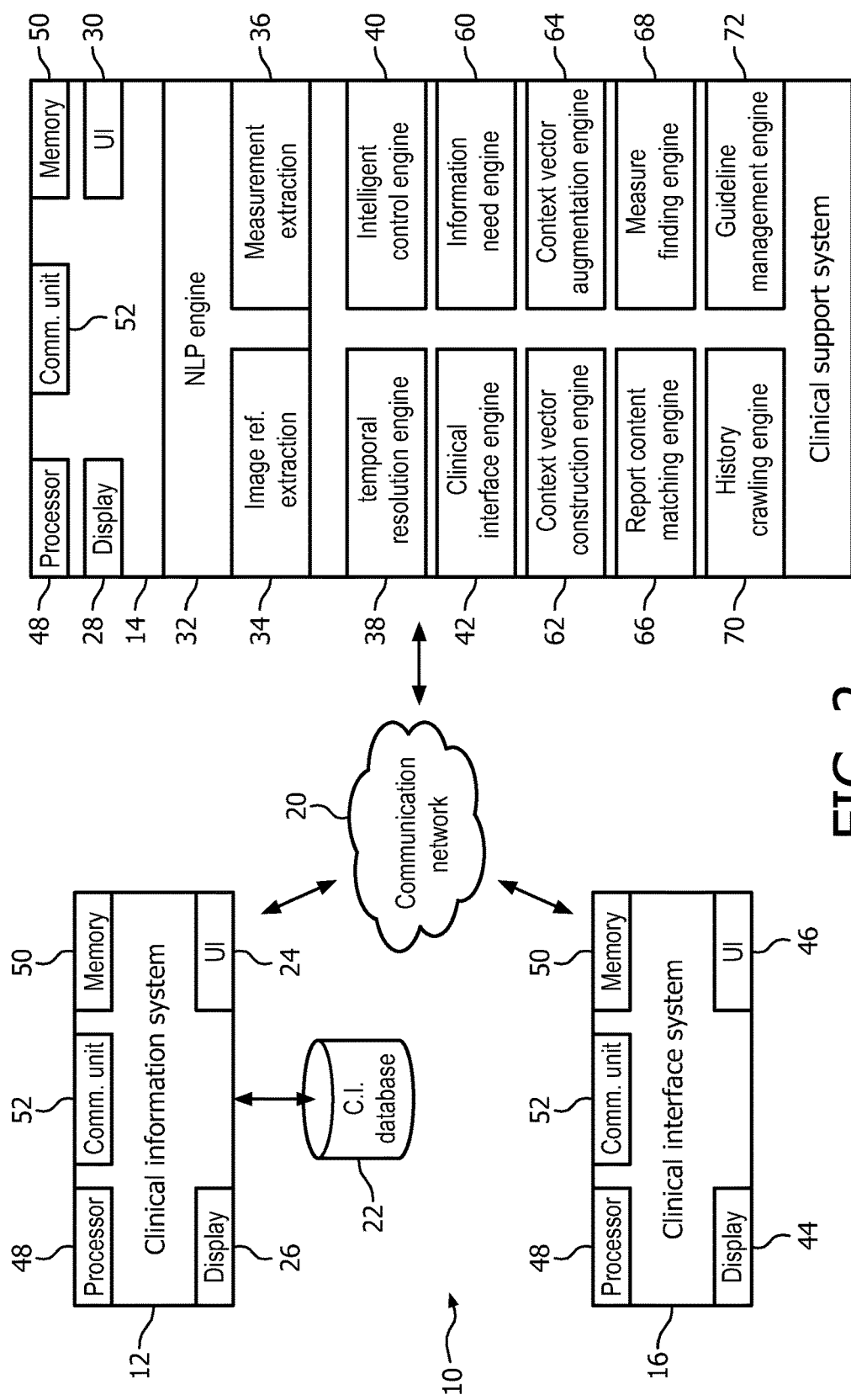
FIG. 2 illustrates a block diagram of an IT infrastructure of a medical institution according to aspects of the present application.

With reference to FIG. 2, a block diagram illustrates one embodiment of an IT infrastructure 10 of a medical institution, such as a hospital. The IT infrastructure 10 suitably includes a clinical information system 12, a clinical support system 14, clinical interface system 16, and the like, interconnected via a communications network 20. It is contemplated that the communications network 20 includes one or more of the Internet, Intranet, a local area network, a wide area network, a wireless network, a wired network, a cellular network, a data bus, and the like. It should also be appreciated that the components of the IT infrastructure be located at a central location or at multiple remote locations.

The clinical information system 12 stores clinical documents including radiology reports, clinical study/exam reports, images, imaging reports, electronic health records, EMR data, and the like in a clinical information database 22. A clinical document may comprise documents with information relating to an entity, such as a patient. Some of the clinical documents may be free-text documents, whereas other documents may be structured document. Such a structured document may be a document which is generated by a computer program, based on data the user has provided by filling in an electronic form. For example, the structured document may be an XML document. Structured documents may comprise free-text portions. Such a free-text portion may be regarded as a free-text document encapsulated within a structured document. Consequently, free-text portions of structured documents may be treated by the system as free-text documents. Each of the clinical documents contains a list of information items. The list of information items includes strings of free text, such as phases, sentences, paragraphs, words, and the like. The information items of the clinical documents can be generated automatically and/or manually. For example, various clinical systems automatically generate information items from previous clinical documents, dictation of speech, and the like. As to the latter, user input devices 24 can be employed. In some embodiments, the clinical information system 12 includes display devices 26 providing users a user interface within which to manually enter the information items and/or display clinical documents. In one embodiment, the clinical documents are stored locally in the clinical information database 22. In another embodiment, the clinical documents are stored in nationally or regionally in the clinical information database 22. Examples of patient information systems include, but are not limited to, electronic medical record systems, departmental systems, and the like.

With reference to FIG. 2, the clinical support system 14 processes the clinical documents to detect information items in the clinical documents and to detect normalized image references and/or measurements within the information items. The clinical support system 14 further correlates the clinical documents which include matching image references and/or measurements to determine which clinical document(s) the detected normalized image references and/or measurements belong to. The clinical support system 14 further links the image references and/or measurements to related clinical findings and information which is included in the one or more clinical documents. The clinical support system 14 also determines the longevity of the clinical findings and information with respect to the image references, the measurements, and/or the one or more clinical documents. The clinical support system 14 further generates a user interface which provides a longitudinal view of the related clinical findings and information. The clinical support system 14 includes a display 28 such as a CRT display, a liquid crystal display, a light emitting diode display, to display the information items and user interface and a user input device 30 such as a keyboard and a mouse, for the clinician to input and/or modify the provided information items.

Specifically, the clinical support system 14 includes a natural language processing engine 32 which processes the clinical documents to detect information items in the clinical documents and to detect a pre-defined list of pertinent clinical findings and information such as image references and/or measurements. To accomplish this, the natural language processing engine 32 segments the clinical documents into information items including sections, paragraphs, sentences, and the like. In one example, the natural language processing engine 32 utilizes a maximum entropy classifier that assigns to each end-of-sentence character (".", ":", "!", "?", "\n") one of four labels: end of sentence and sentence is a section header; end of sentence and sentence is the last sentence of a paragraph; end of sentence and sentence is neither a section header nor the last sentence of a paragraph; and not end of sentence. The section headers are normalized with respect to five classes: technique, comparison, findings, impressions and none. Excluding section headers, the sentences are grouped in paragraphs. Each first sentence in a paragraph is compared against a list of paragraph headers (e.g., LIVER, SPLEEN etc). Matching sentences are marked as being a paragraph header. The content of sections can be easily detected using a predefined list of section headers and text matching techniques. Alternatively, third party software methods can be used, such as MedLEE. For example, if a list of pre-defined terms is given, string matching techniques can be used to detect if one of the terms is present in a given information item. The string matching techniques can be further enhanced to account for morphological and lexical variant and for terms that are spread over the information item. If the pre-defined list of terms contains ontology IDs, concept extraction methods can be used to extract concepts from a given information item. The IDs refer to concepts in a background ontology, such as SNOMED or RadLex. For concept extraction, third-party solutions can be leveraged, such as MetaMap. Further, natural language processing techniques are known in the art per se. It is possible to apply techniques such as template matching, and identification of instances of concepts, that are defined in ontologies, and relations between the instances of the concepts, to build a network of instances of semantic concepts and their relationships, as expressed by the free text.

The natural language processor engine 32 includes an image reference extraction engine 34 to extract the image references from the one or more clinical documents. Specifically, the image reference extraction engine 34 analyzes the one or more clinical documents to determine related information items. The content of information items can be easily detected using a predefined list of information items and text matching techniques. For example, a list of pre-defined terms commonly used in image referencing descriptors is utilized by the image reference extraction engine 34 to detect if one or more of the terms are present in the clinical document. Information items related to an image reference are extracted from the clinical documents and processed by the image reference extraction engine 34 to extract the image references from each information item. For instance, the image reference extraction engine 34 will extract series=11, and image=79 from the information item "The left hepatic reference lesion (series number 11, image number 79) measures approximately 6.4×5.4 cm". To accomplish this, the image reference extraction engine 34 may utilize regular expressions to determine the image and series information within the information item. It is also contemplated that the image references extraction engine 34 may be a data driven, machine learning based approach.

Similarly, a measurement extraction engine 36 of the natural language processor engine 32 extracts image measurements within the one or more clinical documents. Specifically, the measurement extraction engine 36 analyzes the one or more clinical documents to recognize measurement descriptors within the information items. The content of information items can be easily detected using a predefined list of measurement descriptors in information items and text matching techniques. For example, a list of pre-defined terms commonly used in measurement descriptors is utilized by the measurement extraction engine 36 to detect if one or more of the terms are present in the clinical document. The measurement extraction engine 36 also normalizes the measurement descriptors with respect to an information item that represents the measurements dimensions in millimeters. This data structure also records derived information, such as the measurement's dimensionality and its volume in mm, $mm^2$ or $mm^3$. To accomplish this, the measurement extraction engine 36 may utilize regular expressions to determine the measurement information within the information item. It is also contemplated that the measurement extraction engine 36 may be a data driven, machine learning based approach.

The clinical support system 14 further includes a temporal resolution engine 38 which determines which of the one or more clinical documents the image references and/or measurements belong to. Specifically, the temporal resolution engine 38 analyzes the one or more clinical documents to determine which clinical documents have matching image references and/or measurements. In one example, the temporal resolution engine 38 utilizes a classification engine to distinguish between descriptors that describe an entity (a measurement or an image reference) on a current or prior clinical document. In another embodiment, the temporal resolution engine 38 searches for keywords such as 'scan', 'study' in conjunction with dates: (a) occurring prior to an entity (e.g., On the Jan. 19, 2010 scan as measured on series 2 image 120 measures 10 mm . . . ), (b) presence of a date after an entity (e.g., . . . lesion size has decreased compared to prior which measured 3 mm on series 601 image 44 on 3, Jun. 2010), and (c) words such as "prior" and "previous" occurring before/after the entity (e.g., . . . measures 3 mm (series 4, image 52), previously 4 mm (series 4, image 32) and . . . on image 17 series 4 of prior study). This particular approach was evaluated in the publication *Using Image References in Radiology Reports to Support Enhanced Report-to-Image Navigation*, T. Mabotuwana, Y. Qian and M. Sevenster, AMIA Annual Symposium, 2013. The content of the clinical documents can be detected using a predefined list of keywords and text matching techniques. The temporal resolution engine 38 also determines to which clinical document a measurement belongs. For instance, in the sentence "Liver lesion measures 1.2×2.3 cm, previously measuring 0.6×1.2 cm" the second measurement belongs to the prior exam, whereas the first belongs to the study the report is associated with. To accomplish this, the temporal resolution engine 38 utilizes a classifier trained to detect which clinical document a measurement belongs. In one implementation, the temporal resolution engine 38 utilizes regular expressions with a statistical decision making layer defined by a maximum entropy model. This particular approach was evaluated in the publication *Classifying Measurements in Dictated, Free-text Radiology Reports*, M. Sevenster, LNCS 7885, 2013.

The natural language processing engine 32 is further utilized to link a particular image reference and/or measurement to a clinical findings and information within a clinical document. Specifically, the natural language processing engine 32 utilizes the outputs from the image reference extraction engine 34, the measurement extraction engine 36, and the temporal resolution engine 38 to determine the position of the occurrences of the image references and/or measurements in the one or more clinical documents, and utilizes the detected information items to determine the location of related clinical findings or information. For instance, from the paragraph: "LIVER, BILIARY TRACT: Probable diffuse fatty liver. Subtle hypodense soft tissue along the subcapsular portion of the liver segment 7 measures 1.1×2.7 cm (series 5, image 25). Previously 3.2×1.3 cm (series 5, image 43)." The natural language processing engine 32 determines the two measurements and image references are related to liver and biliary tract. To accomplish this, the natural language processing engine 32 utilizes a matching criteria extraction algorithm which matches a particular image reference and a measurement to a clinical findings and information within a clinical document. Further, string matching techniques can then be utilized to detect if one of the terms is present in a given information item in the clinical documents. The natural processing engine 32 then generates a link, such as a hyperlink, connecting the particular image reference and/or measurement to a clinical findings and information within a clinical document.

The clinical support system 14 also includes an intelligent control engine 40 which collects all the related clinical findings and information produced over all of the clinical documents and groups the clinical documents by particular finding of interest, such as a lesion and the like. To accomplish this, the intelligent control engine 40 utilizes techniques that analyze the volumetric similarity between measurements of the finding of interest, the semantic similarity between the sentences in which the measurements are described, whether the measurements appear in the paragraphs with the same header, and slice information, and the like. All such parameters can be taken as input to a rule-based system or a statistical method. The resulting output from the intelligent control engine 40 is a cross-report grouping all the related clinical findings and information over all of the clinical documents which relate to a particular finding of interest. For example, the cross report grouping may include clinical findings and information from three consecutive abdomen CT reports relating to a particular lesion. The grouping may also include the measurements and image references which report the registered lesion on that date's CT exam.

The clinical support system 14 also includes a clinical interface engine 42 that generates a user interface that provides the user a finding-centric view of patient findings. Specifically, the clinical interface engine 42 generates a finding-centric longitudinal patient user interface that can be used to establish clinical context and support navigation directly to corresponding key images. In one embodiment, the clinical interface engine 42 generates a user interface that allows the user to easily navigate to the corresponding image, for instance, by double clicking on an image. The user interfaces can be customized according to user preference, for instance, instead of a grid based image layout all the images belonging to a specific finding can be stacked on top of each other.

The clinical interface system 16 displays the user interface such that the user may view the generated user interfaces. The clinical interface system 16 receives the user interface and displays the view to the caregiver on a display 44. The clinical interface system 16 also includes a user input device 46 such as a touch screen or keyboard and a mouse, for the clinician to input and/or modify the user interface views. Examples of caregiver interface system include, but are not limited to, personal data assistant (PDA), cellular smartphones, personal computers, or the like.

The components of the IT infrastructure 10 suitably include processors 48 executing computer executable instructions embodying the foregoing functionality, where the computer executable instructions are stored on memories 50 associated with the processors 48. It is, however, contemplated that at least some of the foregoing functionality can be implemented in hardware without the use of processors. For example, analog circuitry can be employed. Further, the components of the IT infrastructure 10 include communication units 52 providing the processors 48 an interface from which to communicate over the communications network 20. Even more, although the foregoing components of the IT infrastructure 10 were discretely described, it is to be appreciated that the components can be combined.

Figure 3:
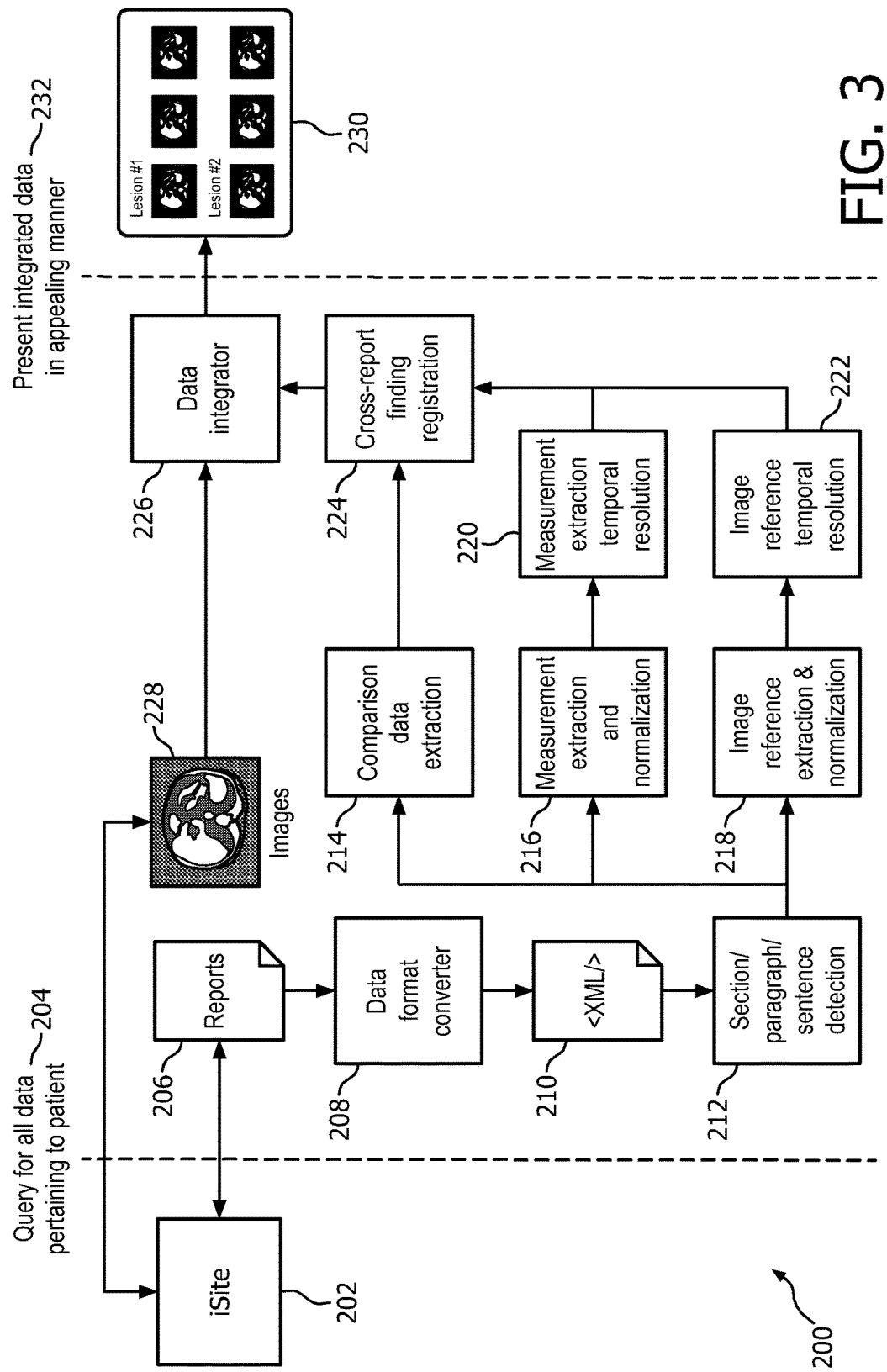
FIG. 3 illustrates a flowchart diagram of the operation of a clinical support system according to aspects of the present application.

With reference to FIG. 3, an exemplary flowchart diagram 200 of the operation of a clinical support system is illustrated. Although each of the blocks in the diagram is described sequentially in a logical order, it is not to be assumed that the system processes the described information in any particular order or arrangement. Clinical documents and images stored in a database (e.g., a Picture Archiving and Communication System such as iSite) 202 are queried for all data pertaining to a particular patient at 204. The clinical documents 206 pertaining to a particular patient are gathered and processed by a data format converter 208 to convert the clinical documents to a common data format 210, such as XML. The clinical documents in the chosen format 210 are then processed by a natural language processor 212 to detect information items such as sections, paragraphs, sentences, and the like. The detected information items in the clinical documents are then processed to extract comparison data 214 within the clinical documents. The information items in the clinical documents are also processed to extract and normalize measurement data 216 and image reference data 218. The measurement data and image reference data are then processed to determine the temporal resolution of the measurement data 220 and image reference data 222, in other words, to determine which clinical documents the measurement data and image reference data belong to. The comparison data, measurement data, and image reference data are then registered in a cross-report grouping of the clinical findings 224. The cross-report grouping of the clinical findings is then integrated 226 with the images 228 pertaining to the particular patient to generate a user interface 230 presenting the integrated data in an appealing manner 232.

With reference to FIG. 4, an exemplary embodiment of a longitudinal view of patient findings interface 300 generated by the clinical support system is illustrated. The interface 300 includes clinical findings and information from three clinical documents relating to a particular finding of interest. Specifically, clinical findings and information 302 from three different clinical documents 304 are displayed. The measurements 306 and image references 308 with matching colors (light gray, dark gray and gray) report the registered finding on each particular clinical document, i.e. date's CT exam. The underlined measurements 310 refer to a measurement or image reference made on the prior exam. The interface 300 also enables the user to click on any of the clinical documents, measurements, and/or image references to display the entire clinical document to which it belongs.

In another embodiment and with continued reference to FIG. 2, the clinical support system 14 determines whether a clinical finding has been identified on a previous clinical document and whether the clinical finding had been previously diagnosed. Specifically, the clinical support system 14 creates an "information needed event" in the case where a clinical finding has been identified on a current clinical document. The clinical support system 14 also generates a context vector which stores information related to a given state of the diagnostic workflow relating to the identified clinical finding. The clinical support system 14 parses the context vector and augments it with data generated by secondary algorithms and/or extracted from the clinical information database 12. The clinical support system 14 then matches the context vector against the content of the current clinical document and singles out pertinent information items from previous clinical documents and displays the pertinent information items via a user interface.

Specifically, the clinical support system 14 includes an information need engine 60 which creates an "information needed event" in the case where a clinical finding has been identified on a current clinical document. The "information need event" could be detected automatically via the natural language processing engine 32 or via a combination of keys or an extra button or menu item in a user interface. In response to detecting an "information need event," a context vector construction engine 62 of the clinical support system 14 generates a context vector which stores information related to a given state of the diagnostic workflow corresponding to the identified clinical finding. Specifically, the context vector construction engine 62 collects digital values from the PACS (Picture Archiving and Communication System) viewing environment, including study ID; patient gender; IDs of series that are open; serial numbers and orientation (axial, sagittal, coronal) of images that are open; DICOM header information (e.g., study/protocol description, window type such as "lungs", "liver"), measurements, other annotations made on images, and the like. It is also contemplated that the context vector construction engine 62 can augment the context vector with the output of eye-tracking software and image processing algorithms. The context vector construction engine 62 harvests all the contextual information available and stores it in a contextual vector. A context vector is a data structure that stores information about a given state of the diagnostic workflow at a particular time.

The clinical support system 14 also includes a context vector augmentation engine 64 that augments the context vector and subsequently manipulates its content with respect to background knowledge. For example, if a database of structured image content is available that has one or more columns in common with a context vector from a similar type of clinical document, the database can be queried for rows that match the context vector's values. For instance, if the context vector has "slice #=53" and "mrn=123456" and the database has a row with (mrn="123456", slice #="53", "date"="Jan. 1, 2001", description="segment 7 liver lesion"), the context vector augmentation engine 64 augments the context vector with "Jan. 1, 2001" and "segment 7 liver lesion". This row serves as a simplified illustration. In practice, the context vector augmentation engine 64 matches with additional information such as date of study and type of study (modality/anatomy). If clinical finding tracking software is being utilized, measurable findings are being stored in such a structured manner. In the course of the human annotation process, measurable findings are stored in terms of measurement dimensions; slice of annotation; date of study; slice thickness; image and series number. Although the database contains information about prior examinations, the context vector augmentation engine 64 utilizes the information by estimating slices. If it is assumed that patients' scans do not show a lot of variability (patients do not change in height; starting point of scanning is grossly the same; protocols are identical over time), then the context vector augmentation engine 64 queries the clinical finding tracking software database for the current slice number (e.g. 53) and neighboring numbers (e.g., the range 50-56). In another embodiment, the context vector augmentation engine 64 utilizes secondary algorithms to augment the context vector. For example, the context vector or parts of it can be handed over to a secondary algorithm that produces one or more additional data items. As an example, an algorithm estimates the organ from a slice number and possibly additional information such as patient gender, slice thickness and number of slices. The problem can be defined as a multi-class classification problem. Specifically, the problem involved determines the organs (e.g., spleen, liver, bladder) to which a given list of pertinent information (slice number, etc.) belong to. So concretely, the algorithm would be given a slice number, e.g., 50 and possibly other information, and return a list of organs associated with that slice number such as "lungs and pleura," "mediastinum and hila," "chest wall," "bones soft tissue," and the like.

The clinical support system 14 also includes a report content matching engine 66 which matches information in the context vector with information items in prior clinical documents. The report content matching engine 66 pre-processes, extracts and normalizes the content from the clinical document, which is then utilized for matching using natural language processing techniques based on rule-based or statistical methods. Typical pre-processing steps include information item detection. For example, the report content matching engine 66 queries the clinical document's meta-information for all information items in the "lungs and pleura" paragraph. If the context vector contains "lungs and pleura" in its list of organs, then the sentences that are obtained in this manner are likely to be of interest in the current context. Image references are also one type of information that can be extracted from clinical documents. The image references are normalized with respect to (image #, series #, date). If the context vector contains identical information, the information in which the original image reference appears is likely to be of interest in the current context. Key phrases can also be filtered from individual information items by means of natural language processing techniques such as string splitting, stemming, chunking, phrase detection and ontological concept extraction techniques. The report content matching engine 66 cycles through all information items in the clinical documents and checks if the information items (partially) match linguistic phrases in the context vector ("segment 7 cyst"), which may have been subjected to the same processing steps as the clinical document content. Sentences that match a phrase are likely to be of interest in the current context. The report content matching engine 66 compiles a list of all information items considered pertinent (i.e., context sensitive).

The clinical interface engine 42 generates a user interface that includes the list of all information items which are considered pertinent. Specifically, the clinical interface engine 42 generates a pertinent information interface that displays the pertinent information items overlaid on the viewing environment. In one embodiment, the text would be "clickable" in which case the entire clinical document is displayed with the initial sentences highlighted in an appropriate format.

Figure 5:
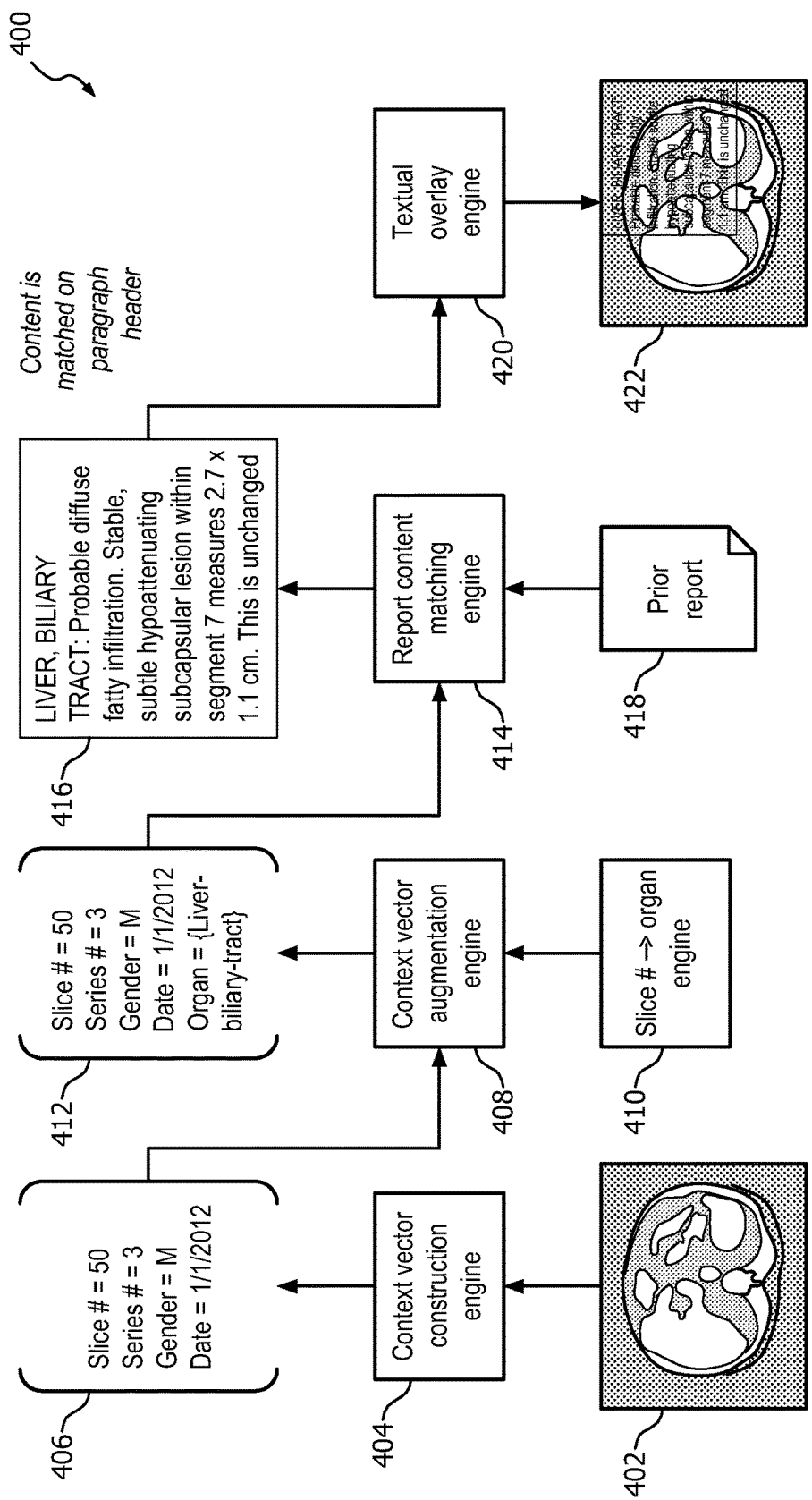
FIG. 5 illustrates another exemplary flowchart diagram of the operation of a clinical support system according to aspects of the present application.

With reference to FIG. 5, another exemplary flowchart diagram 400 of operation of a clinical support system is illustrated. Specifically, FIG. 5 illustrates a flowchart diagram of the clinical support system generating a pertinent information interface. Although each of the blocks in the diagram is described sequentially in a logical order, it is not to be assumed that the system processes the described information in any particular order or arrangement. An image 402 with a measurement is provided to a context vector construction engine 404 which generates a context vector 406 including information related to a given state of the diagnostic workflow. The context vector 406 is then processed by a context vector augmentation engine 408 which parses the context vector and augments it with image reference information and organ information 410 to generate an augmented context vector 412. The augmented context vector 412 is processed by a report content matching engine 414 which matches the augmented context vector 412 against the content of a clinical document 416. The report content matching engine 414 extracts pertinent information items 418 from the clinical document. A textual overlay engine 420 generates an interface 422 in which the pertinent information item is overlaid on the image.

Figure 6:
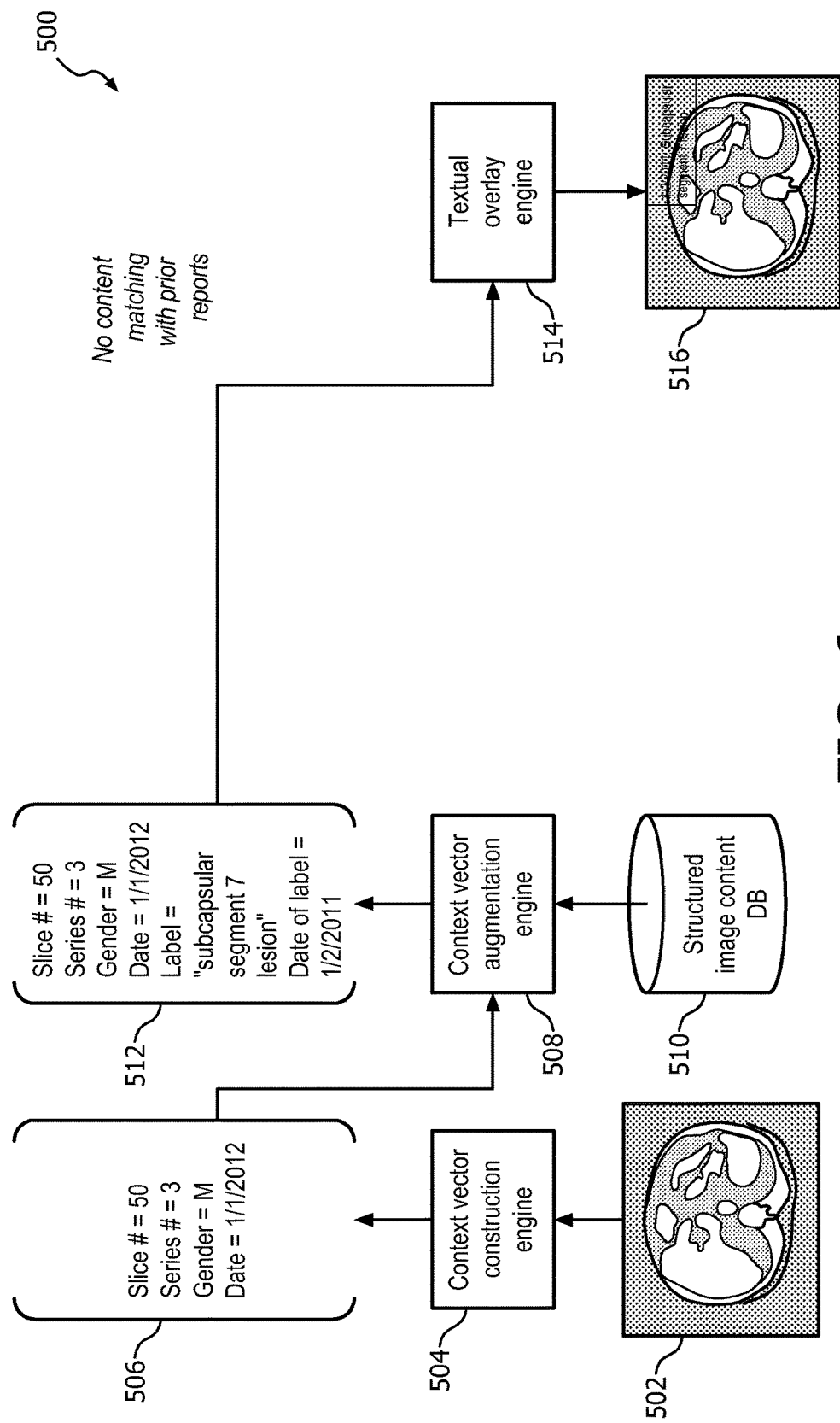
FIG. 6 illustrates another exemplary flowchart diagram of the operation of a clinical support system according to aspects of the present application.

With reference to FIG. 6, another exemplary flowchart diagram 500 of operation of a clinical support system is illustrated. FIG. 6 illustrates another flowchart diagram of the clinical support system generating a pertinent information interface. Although each of the blocks in the diagram is described sequentially in a logical order, it is not to be assumed that the system processes the described information in any particular order or arrangement. An image 502 with a measurement is provided to a context vector construction engine 504 which generates a context vector 506 including information related to a given state of the diagnostic workflow. The context vector 506 is then processed by a context vector augmentation engine 508 which parses the context vector and augments it with image information from a structured image content database 510 to generate an augmented context vector 512. The augmented context vector 512 is provided to a textual overlay engine 514 which generates an interface 516 in which the pertinent information from the augmented context vector 512 is overlaid on the image.

Figure 7:
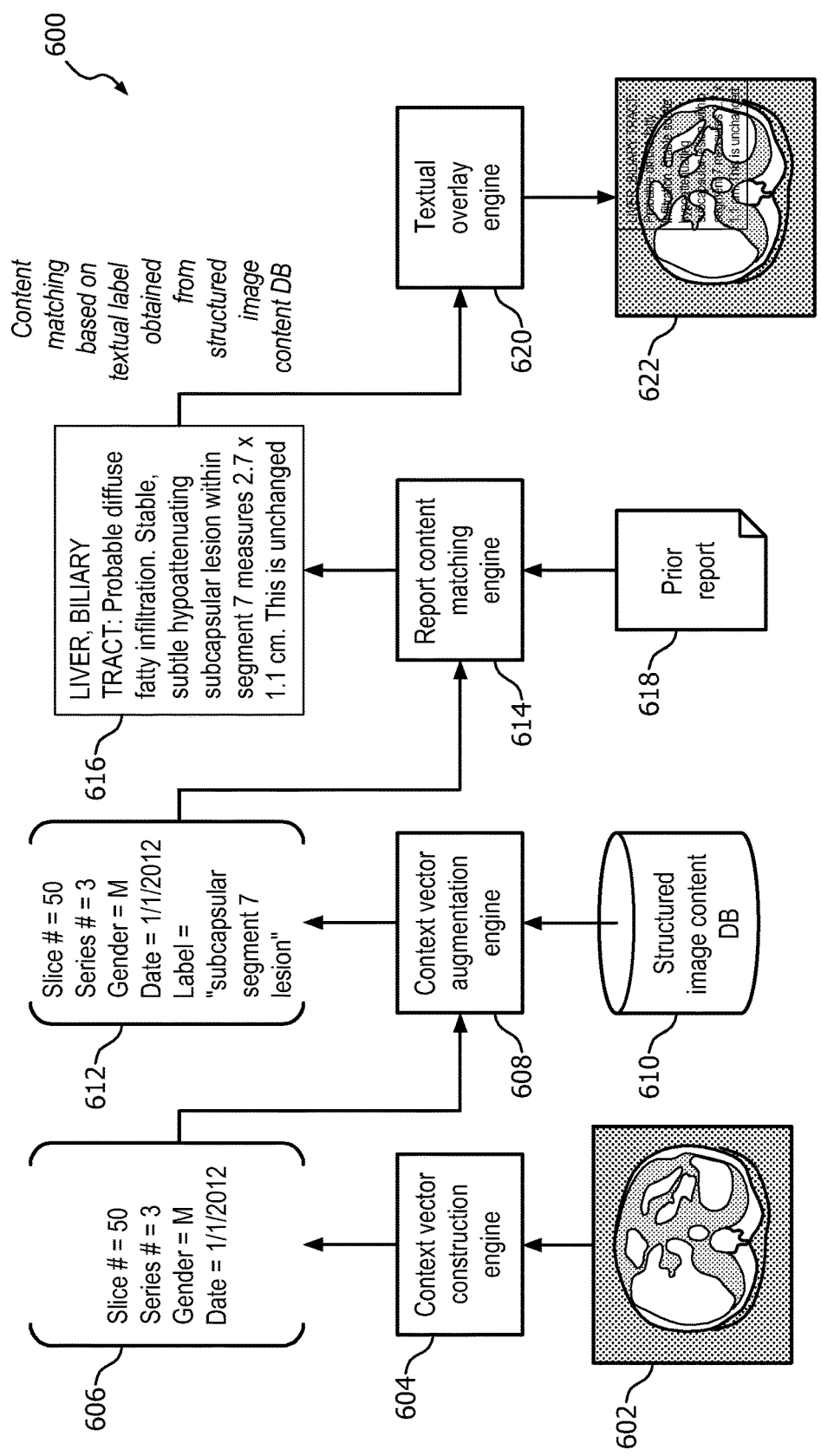
FIG. 7 illustrates another exemplary flowchart diagram of the operation of a clinical support system according to aspects of the present application.

With reference to FIG. 7, another exemplary flowchart diagram 600 of operation of a clinical support system is illustrated. FIG. 7 illustrates another flowchart diagram of the clinical support system generating a pertinent information interface. Although each of the blocks in the diagram is described sequentially in a logical order, it is not to be assumed that the system processes the described information in any particular order or arrangement. An image 602 with a measurement is provided to a context vector construction engine 604 which generates a context vector 606 including information related to a given state of the diagnostic workflow. The context vector 606 is then processed by a context vector augmentation engine 608 which parses the context vector and augments it with image information from a structured image content database 610 to generate an augmented context vector 612. The augmented context vector 612 is processed by a report content matching engine 614 which matches the augmented context vector 612 against the content of a clinical document 616. The report content matching engine 614 extracts pertinent information items 618 from the clinical document. A textual overlay engine 620 generates an interface 622 in which the pertinent information item is overlaid the image.

Figure 8:
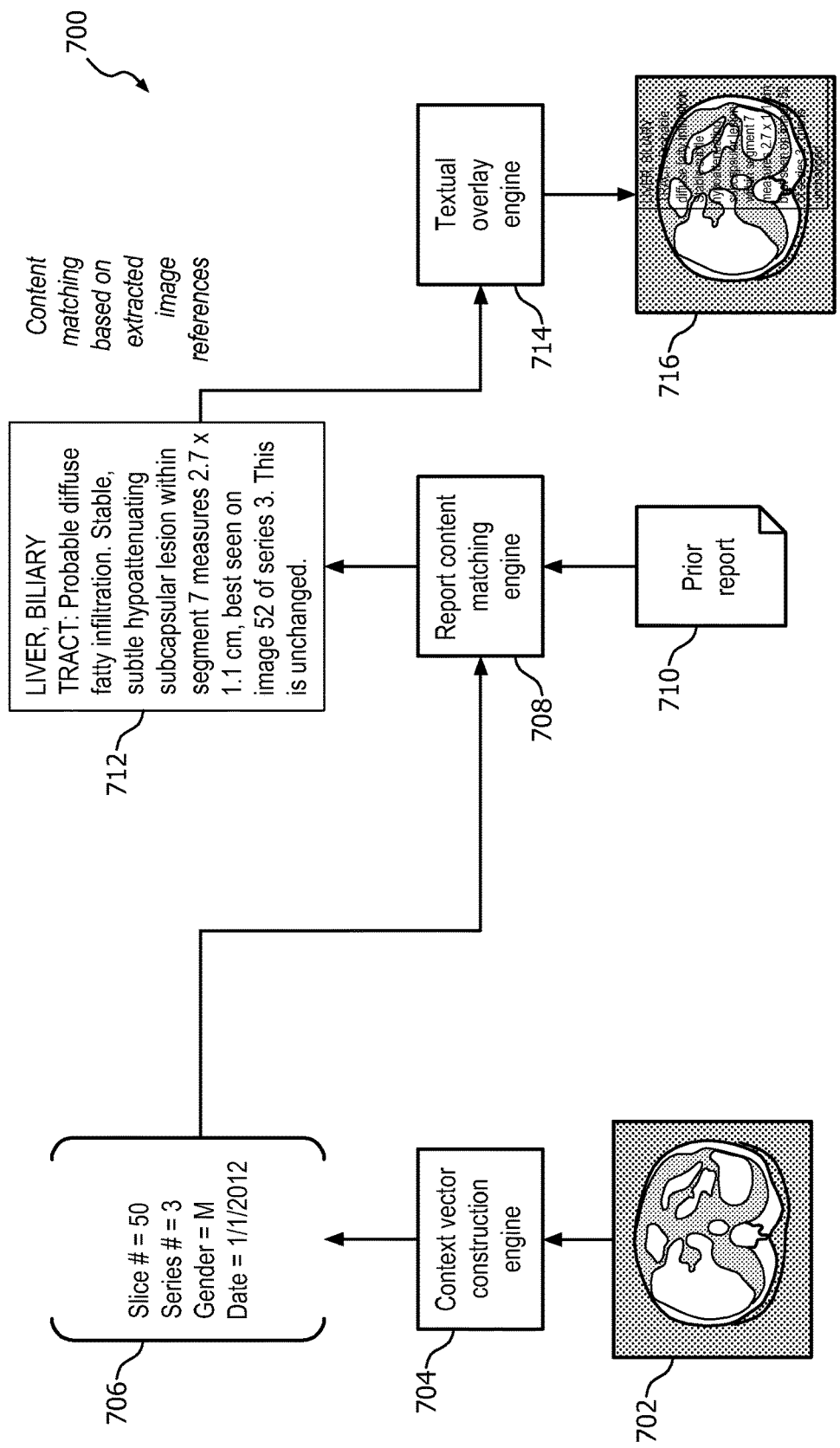
FIG. 8 illustrates another exemplary flowchart diagram of the operation of a clinical support system according to aspects of the present application.

With reference to FIG. 8, another exemplary flowchart diagram 700 of operation of a clinical support system is illustrated. FIG. 8 illustrates another flowchart diagram of the clinical support system generating a pertinent information interface. Although each of the blocks in the diagram is described sequentially in a logical order, it is not to be assumed that the system processes the described information in any particular order or arrangement. An image 702 with a measurement is provided to a context vector construction engine 704 which generates a context vector 706 including information related to a given state of the diagnostic workflow. The context vector 706 is processed by a report content matching engine 708 which matches the context vector 706 against the content of a clinical document 710. The report content matching engine 708 extracts pertinent information items 712 from the clinical document 710. A textual overlay engine 714 generates an interface 716 in which the pertinent information item is overlaid on the image.

In another embodiment and with continued reference to FIG. 2, the clinical support system 14 provides an assessment of the interval change of measured findings in previous clinical documents and displays the interval change in a consistent guideline-compliant manner. Specifically, the clinical support system 14 listens to the application programming interface (API) of a PACs viewing environment and determines if a clinical finding is being measured. If a clinical finding is being measured, the clinical support system 14 transmits an alarm to the user indicating that the measurement corresponds to a particular finding. The clinical support system 14 further collects clinical findings and information about a given region of interest (e.g. an open image) and stores it in a context vector. The clinical supports system 14 retrieves measurements from one or more clinical document stored in the clinical information system 12. One or more interval change terminology guidelines are applied to the retrieved measurements by the clinical support system 14 to provide a qualitative assessment of the interval change of measured findings in previous clinical documents.

Specifically, the clinical support system 14 includes a measured finding engine 68 which determines if a particular clinical finding is being measured. Specifically, the measured finding engine 68 determines if two or more measurements pertain to the same clinical finding. To accomplish this, the measured finding engine 68 utilizes one or more rule sets or algorithms to determine whether two or more measurements are related to a similar clinical finding. For example, the measured finding engine 68 determines if two measurements were made within a predetermined time period. If the measurements were made within the predetermined time period, the measured finding engine 68 determines that the measurements relate to the same clinical finding. If the measurements are not made within the predetermined time period, the measured finding engine 68 determines that the measurements are not related. Specifically, whenever a measurement is made, the measured finding engine 68 searches for another measurement made within a predetermined time period. If no other measurements are made within this time interval, the measured finding engine 68 determines that the measurement pertains to a particular finding and issues an alert to the user. The alert is issued to notify the user that all of the measurement associated with a clinical finding have been detected.

The context vector construction engine 62 of the clinical support system 14 generates a context vector which stores information related to a given state of the diagnostic workflow relating to the identified clinical finding. Specifically, the context vector construction engine 62 collects digital values from the PACS viewing environment, including study ID; patient gender; IDs of series that are open; serial numbers and orientation (axial, saggital, coronal) of images that are open; DICOM header information (e.g., study/protocol description, window type such as "lungs", "liver"), measurements, other annotations made on images, and the like.

The clinical support system 14 also includes a finding history crawling engine 70 which retrieves measurements related to related clinical findings and information from one or more clinical documents. For example, the finding history crawling engine 70 singles a clinical finding in the clinical information database 12 that corresponds with the measured entity in the region of interest based on the context vector. It should be contemplated that this can be fully automated or require user intervention. In this scenario, whenever an alert is issued, the finding history crawling engine 70 complies a list of objects from the clinical information database 12 possibly with labels that describe each object ("segment 7 lesion"). The user selects the measured entity from a list of objects retrieved from the clinical information database 12. When the user selects an object from the list it is understood that this is the object that is associated with the measured entity in the region of interest. In another embodiment, the clinical information database 12 is populated by means of special devices integrated in the viewing environment. Clinical finding tracking software is such a workflow device. In the clinical finding tracking software, each clinical finding object contains one or more measurements made on a clinical document grouped by date. In addition, each clinical finding object has a descriptive label ("segment 7 lesion"). Alternatively, measurements are extracted from one or more clinical documents and grouped by finding. Natural language processing techniques can be used to achieve this. For instance, consider the following time-stamped sentences that were taken from three consecutive reports:

Mar. 4, 2005: Subtle hypodense soft tissue along the subcapsular portion of the liver segment 7 measures 1.1×2.7 cm.

Apr. 5, 2006: Stable, subtle hypoattenuating subcapsular lesion within segment 7 measures 2.7×1.1 cm.

May. 6, 2007: Hypodense lesion within segment 7 of the liver now measures 3.5×1 cm, previously measuring 2.7×1.1 cm.

The natural language processing engine 32 groups the underlined measurements together, recognizing that the measurements quantify the same clinical finding. The natural language processing engine 32 is also utilized to generate a descriptive label from these sentences, for instance the natural language processing engine 32 would apply chunking and concept extraction techniques. The natural language processing engine 32 then recognizes that the phrases "subcapsular portion of the liver segment 7" and "Hypodense lesion within segment 7 of the liver" describe the same finding. Since a considerable number of words in these phrases overlap, the finding history crawling engine 70 determines the descriptive label of that finding, and present one or all as descriptors of the finding in the structured database. In another embodiment, the finding history crawling engine 70 includes a query mechanism to obtain the measurements associated with the selected clinical finding object. The query result can be maintained internally as a mapping between exam dates and measurements. Additional data can further be included, such as image and series numbers, see Table 1, depending on availability in the database.

TABLE 1

| Date | X (in mm) | Y (in mm) | Z (in mm) | Image | Series |
|---|---|---|---|---|---|
| Jan. 1, 2001 | 12 | 11 | | 51 | 3 |
| Jan. 1, 2002 | 12 | 11 | | 49 | 3 |
| Jan. 1, 2003 | 14 | 13 | | 52 | 3 |
| Jan. 1, 2004 | 15 | 14 | | 51 | 3 |
| Jan. 1, 2005 | 17 | 15 | | 48 | 3 |

The clinical support system 14 further includes a guideline management engine 72 which provides a qualitative assessment of the interval change of measured findings in the previous clinical documents. An implementation of a guideline can be considered as a set of rules of the form: If <measurement equation 1> and . . . and <measurement equation K> then <assessment>. Here, <measurement equation i> stands for an algebraic equation involving measurement data, such as "longest diameter on current exam/longest diameter on prior exam >1.2"; and <assessment> stands for "stable" or "decreased", etc. The guideline management engine 72 selects one or more guidelines based on the context vector. Pertinent guidelines are the World Health Organization guideline and the RECIST guideline (Response Evaluation Criteria In Solid Tumors). The guideline management engine 72 further applies rules in the selected guidelines to the obtained measurements and clinical information. In case more information is required to apply a rule in the selected guideline, the information can be obtained from the context vector, secondary algorithms applied to data in the context vector, or direct transmission by the user. For instance, the RECIST guideline distinguishes between tumors and lymph nodes. The natural language processing engine 32 can be constructed to classify if a finding is a tumor or a lymph node, based on measurement and its descriptive label ("segment 7 lesion"→tumor; "right hilar lymph node"→lymph node). The natural language processing engine 32 can use string matching techniques as well as statistical feature integration and concept mapping techniques. The predicted class can be shown to the user for approval. The guidelines can be applied on the current clinical document and its most recent prior or an earlier clinical document.

The clinical interface engine 42 generates a user interface that visualizes the obtained measurements as an overlay or popup in the region of interest. In an advanced embodiment, the "dots" on the graphical time line are entry points for opening up image information, e.g., a key image on which the prior measurement appears. The clinical interface engine 42 is also very suitable for supporting referring physicians. The rich yet concise interface of the current appearance and its progression over time can be shown on a small single-screen device. The graph could potentially be used to navigate through time and show earlier images. Also alternative interfaces can be envisaged—e.g. a multi-image matrix where the clinical interface engine 42 utilizes information to show the clinical finding progression over time with the images zoomed and panned such that the clinical finding progression can also be appreciated visually.

Figure 9:
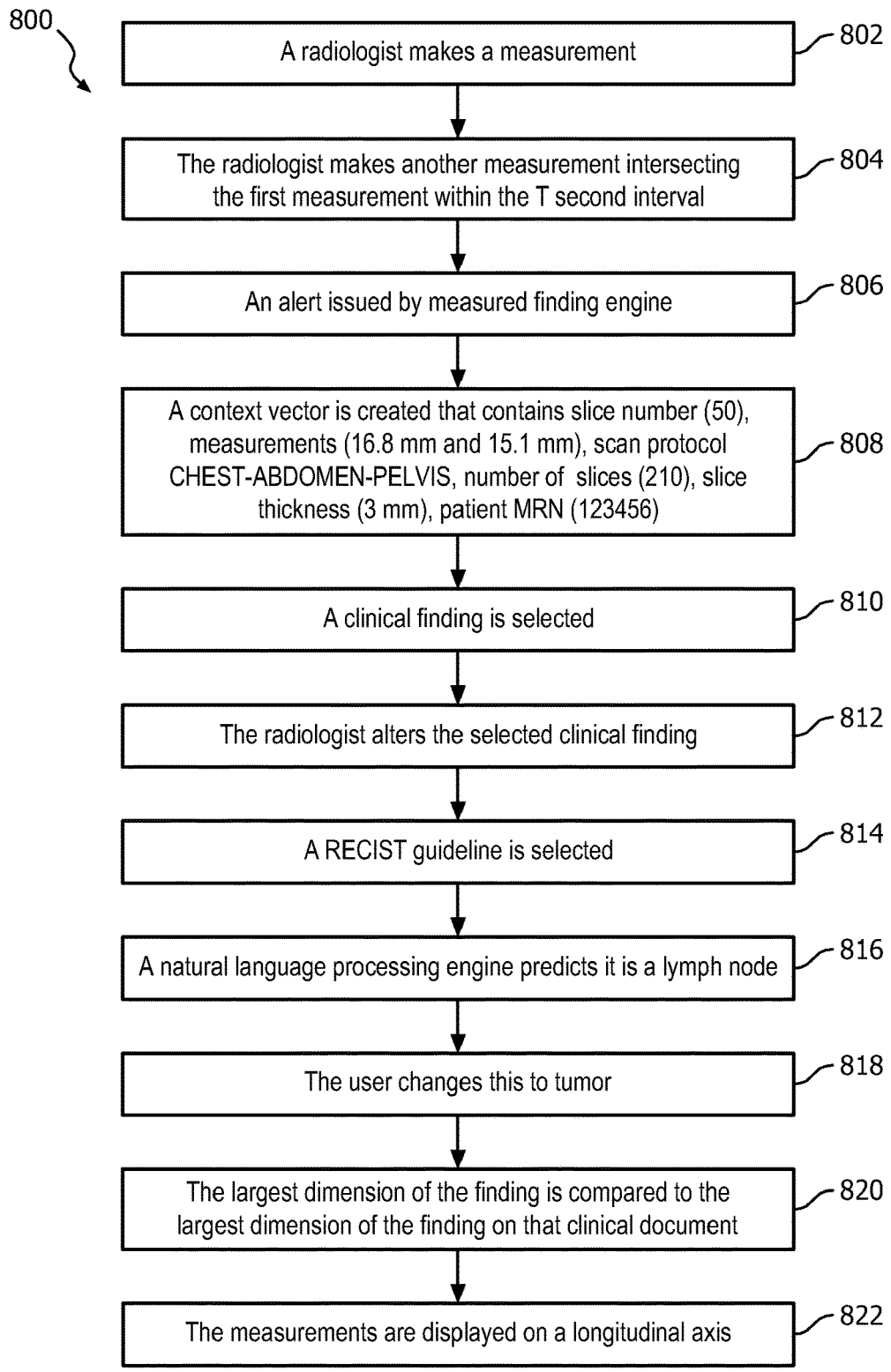
FIG. 9 illustrates another exemplary flowchart diagram of the operation of a clinical support system according to aspects of the present application.

With reference to FIG. 9, another exemplary flowchart diagram 800 of operation of a clinical support system is illustrated. In a step 802, a radiologist makes a measurement. In a step 804, the radiologist makes another measurement intersecting the first measurement within the T second interval. In a step 806, an alert is issued by measured finding engine. In a step 808, a context vector is created that contains slice number (50), measurements (16.8 mm and 15.1 mm), scan protocol CHEST-ABDOMEN-PELVIS, number of slices (210), slice thickness (3 mm), patient MRN (123456). In a step 810, a clinical finding is selected. This is the incorrect lesion, in a step 812, the radiologist alters the selected clinical finding. The label of the currently selected clinical finding object is "segment 7 lesion". Since this is a CHEST-ABDOMEN-PELVIS study, the RECIST guideline is selected in a step 814. To apply the RECIST guideline, the guideline management engine needs to know if the lesion is a tumor or a lymph node. A natural language processing engine predicts it is a lymph node in a step 816. The user changes this to tumor in a step 818. For each clinical document, per RECIST guideline, the largest dimension of the finding is compared to the largest dimension of the finding on that clinical document in a step 820. With regards to the most recent prior (Jan. 1, 2005), the clinical document is stable; however, with regards to the study Jan. 1, 2003 there is progressed disease. The measurements are displayed on a longitudinal axis on a step 822. The qualitative assessment is displayed on the screen as well.

Figure 10:
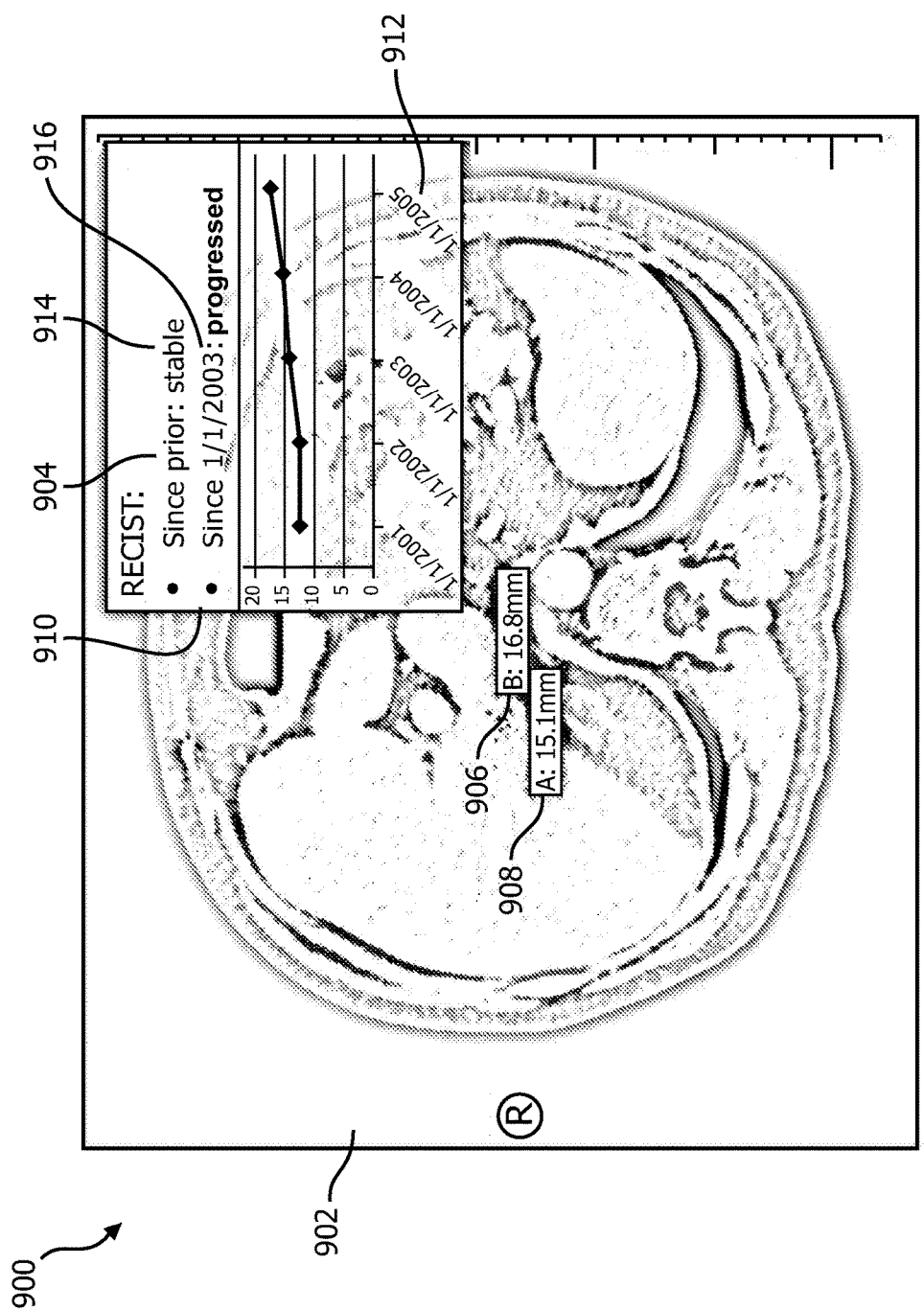
FIG. 10 illustrates an exemplary embodiment of a qualitative assessment interface generated by the clinical support system according to aspects of the present application.

With reference to FIG. 10, an exemplary embodiment of a qualitative assessment interface 900 generated by the clinical support system is illustrated. The interface 900 includes an image 902 and a qualitative assessment sector 904. The image 902 includes measurements 906 for a clinical finding 908. The qualitative assessment sector 904 includes an assessment of the size 910 of the clinical finding over time 912. The qualitative assessment also includes the RECIST status of the clinical finding 914 and the date of the latest exam 916.

Figure 11:
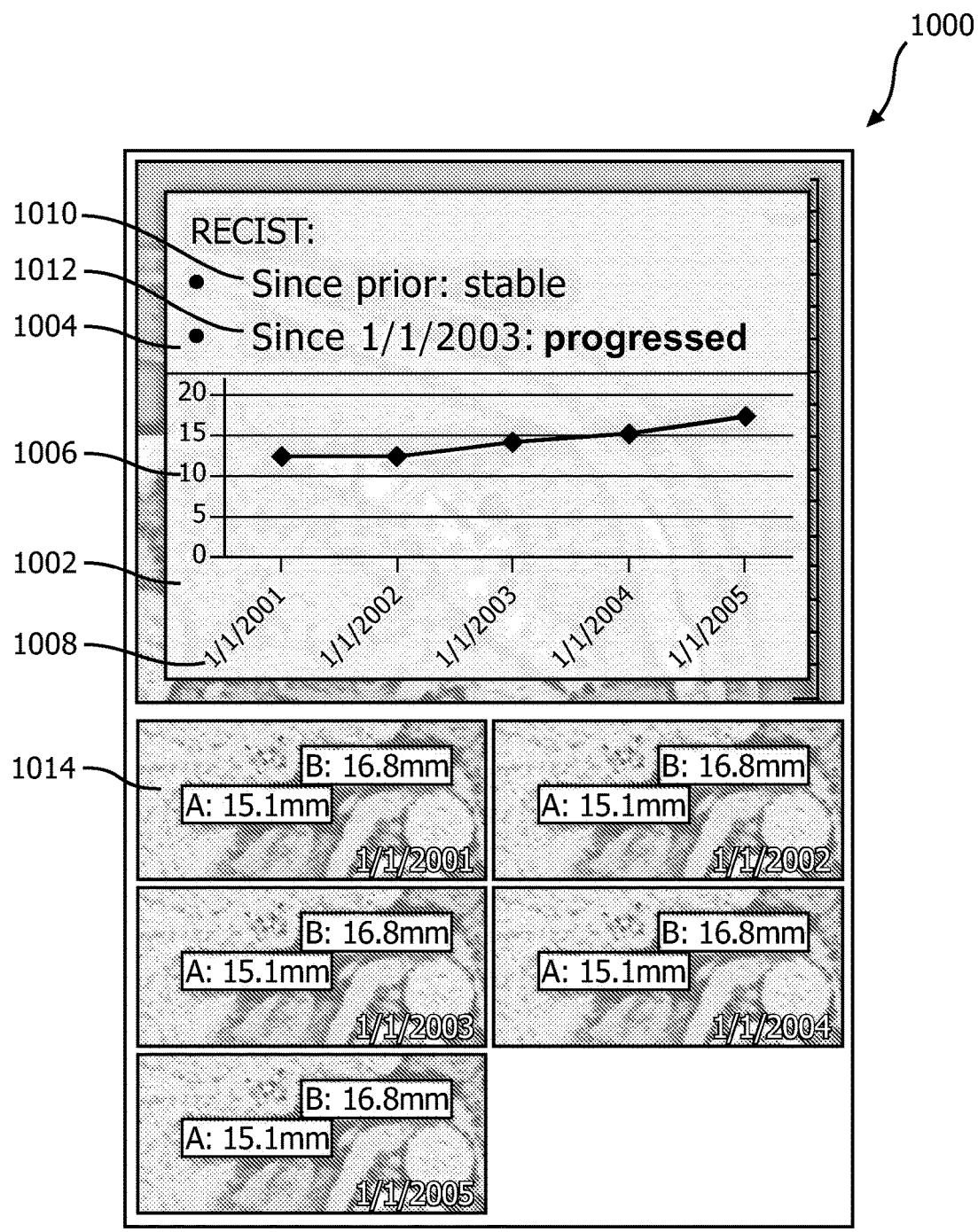
FIG. 11 illustrates another exemplary embodiment of a qualitative assessment interface generated by the clinical support system according to aspects of the present application.

With reference to FIG. 11, an exemplary embodiment of a qualitative assessment interface 1000 generated by the clinical support system is illustrated. The interface 1000 includes an image 1002 and a qualitative assessment sector 1004. The qualitative assessment sector 1004 includes an assessment of the size 1006 of the clinical finding over time 1008. The qualitative assessment also includes the RECIST status of the clinical finding 1010 and the date of the latest exam 1012. The interface 1000 also includes a matrix view 1014 of all clinical finding measurements over time.

Figure 12:
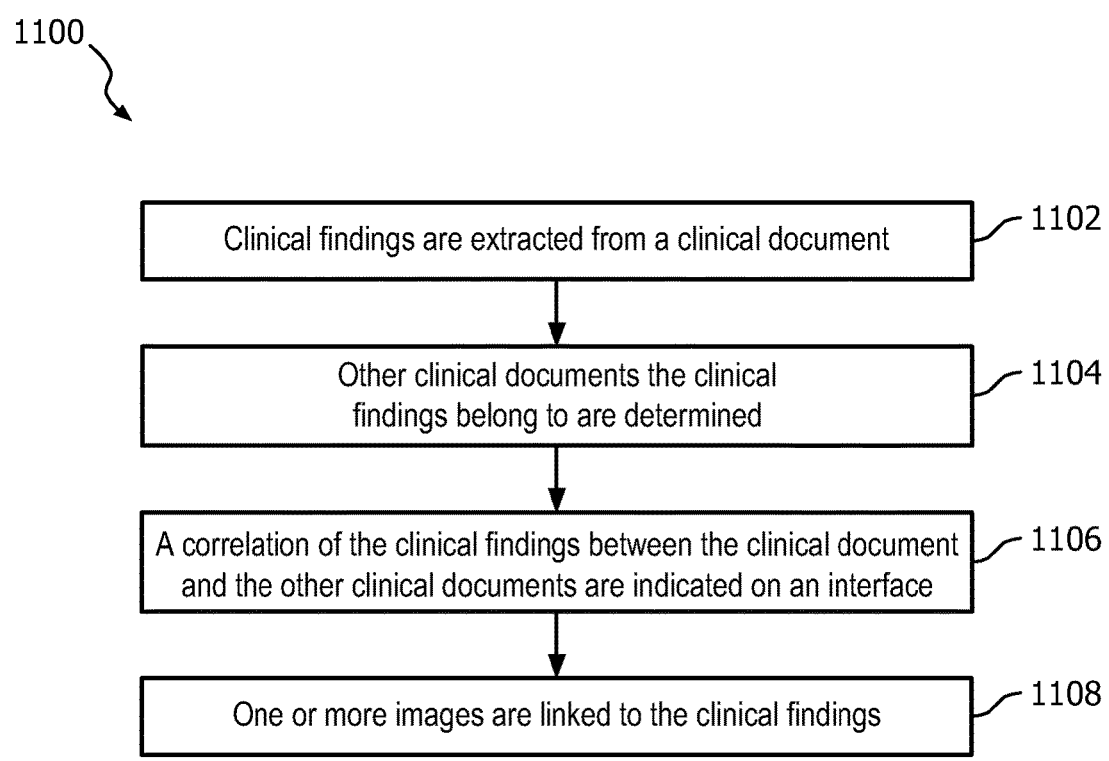
FIG. 12 illustrates a method for automatic creation of a finding-centric longitudinal view of patient findings according to aspects of the present application.

With reference to FIG. 12, a method for automatic creation of a finding-centric longitudinal view of patient findings 1100 is illustrated. Although each of the blocks in the diagram is described sequentially in a logical order, it is not to be assumed that the system processes the described information in any particular order or arrangement. In a step 1102, clinical findings are extracted from a clinical document. In a step 1104, other clinical documents the clinical findings belong to are determined. In a step 1106, a correlation of the clinical findings between the clinical document and the other clinical documents are indicated on an interface. In a step 1108, one or more images are linked to the clinical findings.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), personal data assistant (PDA), cellular smartphones, mobile watches, computing glass, and similar body worn, implanted or carried mobile gear; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system for creating a longitudinal view of patient findings, the system comprising:
   a natural language processor engine which extracts clinical findings from a clinical document;
   a temporal resolution engine which determines which other clinical documents the clinical findings belong to by analyzing the clinical document and the other clinical documents to determine matching image references and measurements between the clinical document and the other clinical documents, and wherein the other clinical documents relate to the patient; and
a visualization graphical user interface which indicates a correlation of the clinical findings between the clinical document and the other clinical documents, wherein the visualization graphical user interface indicates the correlation of the clinical findings by highlighting, in the clinical document and the other clinical documents, measurements matching between the clinical document and the other clinical documents, and image references matching between the clinical document and the other clinical documents;
wherein the natural language processor engine links one or more images to the clinical findings.

2. The system according to claim 1, wherein the natural language process engine extracts measurements and image references from the clinical document and the other clinical documents.

3. The system according to claim 1, further including:
an intelligent control engine which determines a longevity of the measurements and image reference with respect to each clinical finding.

4. The system according to claim 1, further including:
a context vector construction engine which generates a context vector relating to a given state of diagnostic workflow for each clinical finding.

5. The system according to claim 4, further including:
a context vector augmentation engine which parses the context vector and augments it with clinical information extracted from the clinical document.

6. The system according to claim 4, further including:
a report content matching engine which extracts pertinent clinical information relating to the clinical finding from the other clinical documents using the context vector.

7. The system according to claim 1, further including:
a guideline management engine which applies one or more interval change terminology guidelines to the clinical finding to generate a quantitative and/or qualitative assessment of the clinical finding.

8. The system according to claim 1, wherein the visualization graphical user interface displays the clinical findings and a quality assessment with respect to the clinical document and the other clinical documents.

9. The system according to claim 1, wherein the temporal resolution engine is configured to use a trained classifier to determine which other clinical documents the clinical findings belong to.

10. The system according to claim 1, further comprising a measured finding engine which determines whether two or more measurements pertain to the same clinical finding by determining whether the two or measurements have been made within a predetermined time period.

11. A method for creating a longitudinal view of patient findings, the method comprising:
extracting clinical findings from a clinical document;
determining which other clinical documents the clinical findings belong to by analyzing the clinical document and the other clinical documents to determine matching image references and measurements between the clinical document and the other clinical documents, and wherein the other clinical documents relate to the patient;
indicating a correlation of the clinical findings between the clinical document and the other clinical documents on an interface by highlighting, in the clinical document and the other clinical documents, measurements matching between the clinical document and the other clinical documents, and image references matching between the clinical document and the other clinical documents;
linking one or more images to the clinical findings.

12. The method according to claim 11, further including:
extracting measurements and image references from the clinical document and the other clinical documents.

13. The method according to claim 11, further including:
determining a longevity of the measurements and image reference with respect to each clinical finding.

14. The method according to claim 13, further including:
generating a context vector relating to a given state of diagnostic workflow for each clinical finding.

15. The method according to claim 14, further including:
extracting pertinent clinical information relating to the clinical finding from the other clinical documents using the context vector.

16. The method according to claim 11, further including:
applying one or more interval change terminology guidelines to the clinical finding to generate a qualitative assessment of the clinical finding.

\* \* \* \* \*